United States Patent [19]

Lam

[11] Patent Number: 4,836,942

[45] Date of Patent: Jun. 6, 1989

[54] LUBRICANT COMPOSITION

[75] Inventor: William Y. Lam, Ballwin, Mo.

[73] Assignee: Ethyl Petroleum Additives, Inc., St. Louis, Mo.

[21] Appl. No.: 202,319

[22] Filed: Jun. 6, 1988

[51] Int. Cl.$^4$ ........................................ C10M 135/18
[52] U.S. Cl. .................................... 252/47; 252/402; 558/239; 558/240
[58] Field of Search .................. 252/47, 402; 558/239, 558/240

[56] References Cited

U.S. PATENT DOCUMENTS

| | | | |
|---|---|---|---|
| 3,882,031 | 5/1975 | Askew et al. | 252/47 |
| 3,885,039 | 5/1975 | Pinkowski et al. | 558/240 |
| 4,501,678 | 2/1985 | Katayama et al. | 252/47 |

Primary Examiner—William R. Dixon, Jr.
Assistant Examiner—Jerry D. Johnson
Attorney, Agent, or Firm—John F. Sieberth; David M. Bunnell

[57] ABSTRACT

Compounds or mixtures of compounds having the formulae:

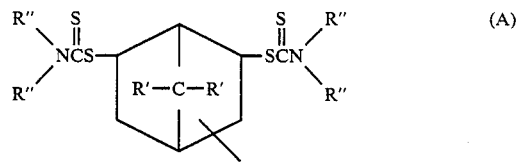

(A)

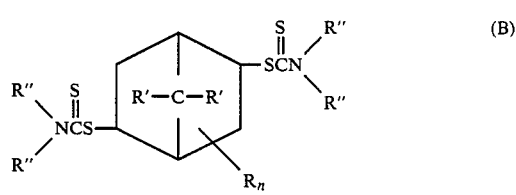

(B)

wherein R is an alkyl group containing from 1 to 20 carbon atoms, n represents a number selected from the class consisting of zero and the integers from 1 through 6, R' represents a member selected from the group consisting of the hydrogen atom and those groups represented by R and R" is an aliphatic hydrocarbon group are effective antiwear and antioxidant additives in lubricating oils.

38 Claims, No Drawings

LUBRICANT COMPOSITION

BACKGROUND OF THE INVENTION

This invention relates to certain novel esters of dithiocarbamic acids. More particularly, this invention relates to certain novel bicycloheptyl esters of dihydrocarbyl dithiocarbamic acids having utility as lubricant additives and lubricating compositions containing them. The invention also relates to a process for preparing such products.

Additives are conventionally added to lubricating oils to improve their properties. Antiwear additives used in the past include compounds such as zinc dialkyldithiophosphates, sulfurized sperm oil, and the like. Antioxidant additives used in the past include sulfurized oil-soluble organic compounds, such as wax sulfides and polysulfides, sulfurized olefins, sulfurized fatty acid esters, and sulfurized olefin esters, as well as oil-soluble phenolic and aromatic amine antioxidants.

SUMMARY OF THE INVENTION

It has now been found that certain bicycloheptyl esters of dihydrocarbyl dithiocarbamic acids are very effective antiwear and antioxidant additives in lubricating compositions such as crankcase lubricants.

DETAILED DESCRIPTION OF THE INVENTION

A preferred embodiment of this invention is an antiwear and antioxidant compound or mixture of compounds having the following general formulae:

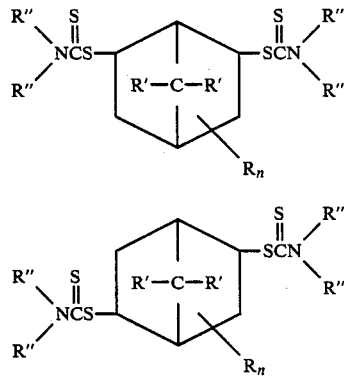

wherein R represents an alkyl group containing from 1 to 20 carbon atoms, n represents a number selected from the class consisting of zero and the integers from 1 through 6, R' represents a member of the group consisting of the hydrogen atom and those groups represented by R and R" represents an aliphatic essentially hydrocarbon group. The term "essentially hydrocarbon group" is used to define a class of substituent groups which includes unsubstituted hydrocarbon groups and substituted hydrocarbon groups in which the substituent groups are such, and are substituted in such position, that they are in effect inert and do not alter significantly the basically hydrocarbon character of the hydrocarbon group. Thus, included within the meaning of the definition given the symbol R" are hydrocarbon groups such as the alkyl and alkenyl groups and their substitution derivatives. It is preferred that the group designated by the symbol R" be an unsubstituted lower alkyl group containing not more than about 12 carbon atoms. Examples of this group include the methyl, ethyl, propyl, hexyl, octyl, decyl, dodecyl, ethenyl, propenyl, butenyl, hexenyl, octenyl and dodecenyl groups.

The novel compounds of the invention may be generically characterized as bicyclo(2.2.1)heptyl-2,6-bis(N,N-dihydrocarbyldithiocarbamates), bicyclo(2.2.1)heptyl-2,5-bis(N,N-dihydrocarbyldithiocarbamates) and their alkyl substitution products. From the general formulae given, it can be seen that the essential configuration of the novel compounds is such that a bicyclo(2.2.1)heptyl racical is attached by a saturated ring carbon atom at the 2-position and 6-position of the ring or at the 2-position and 5-position of the ring to a sulfur atom of a dithiocarbamic acid moiety.

Examples of these novel compounds include:
bicyclo(2.2.1)heptyl-2,6-bis(N,N-dimethyldithiocarbamate),
bicyclo(2.2.1)heptyl-2,6-bis(N,N-diisopropyldithiocarbamate),
bicyclo(2.2.1)heptyl-2,6-bis(N,N-di-n-butyldithiocarbamate),
bicyclo(2.2.1)heptyl-2,6-bis(N,N-dihexyldithiocarbamate),
bicyclo(2.2.1)heptyl-2,6-bis(N,N-didodecyldithiocarbamate),
1,4-dimethylbicyclo(2.2.1)heptyl-2,6-bis(N,N-dimethyldithiocarbamate),
3,5-dimethylbicyclo(2.2.1)heptyl-2,6-bis(N,N-dimethyldithiocarbamate),
1,4-diethylbicyclo(2.2.1)heptyl-2,6-bis(N,N-dimethyldithiocarbamate),
3,5-diethylbicyclo(2.2.1)heptyl-2,6-bis(N,N-dimethyldithiocarbamate),
2,4-diisopropylbicyclo(2.2.1)heptyl-2,6-bis(N,N-di-n-butyldithiocarbamate),
2,4-dioctylbicyclo(2.2.1)heptyl-2,6-bis(N,N-di-n-butyldithiocarbamate),
2,4-didecylbicyclo(2.2.1)heptyl-2,6-bis(N,N-di-n-butyldithiocarbamate),
2,5-dimethylbicyclo(2.2.1)heptyl-2,6-bis(N,N-dihexyldithiocarbamate),
2,6-dimethylbicyclo(2.2.1)heptyl-2,6-bis(N,N-dioctyldithiocarbamate),
1,3,5-trimethylbicyclo(2.2.1)heptyl-2,6-bis(N,N-didecyldithiocarbamate),
2,4,6-triethylbicyclo(2.2.1)heptyl-2,6-bis(N,N-didodecyldithiocarbamate),
1,4,5,6,7,7-hexamethylbicyclo(2.2.1)heptyl-2,6-bis(N,N-di-n-butyldithiocarbamate),
7,7-dimethylbicyclo(2.2.1)heptyl-2,6-bis(N,N-dimethyldithiocarbamate),
bicyclo(2.2.1)heptyl-2,6-bis(N-methyl-N-ethyldithiocarbamate),
bicyclo(2.2.1)heptyl-2,6-bis(N-methyl-N-propyldithiocarbamate),
bicyclo(2.2.1)heptyl-2,6-bis(N-methyl-N-octyldithiocarbamate),
bicyclo(2.2.1)heptyl-2,6-bis(N-ethyl-N-hexyldithiocarbamate),
bicyclo(2.2.1)heptyl-2,6-bis(N-propyl-N-dodecyldithiocarbamate),
1,4-dimethylbicyclo(2.2.1)heptyl-2,6-bis(N-methyl-N-ethyldithiocarbamate),
3,5-dimethylbicyclo(2.2.1)heptyl-2,6-bis(N-methyl-N-propyldithiocarbamate),
1,4-diethylbicyclo(2.2.1)heptyl-2,6-bis(N-methyl-N-octyldithiocarbamate), 3,5-diethylbicyclo(2.2.1)heptyl-2,6-bis(N-ethyl-N-hexyldithiocarbamate),
2,4-dimethylbicyclo(2.2.1)heptyl-2,6-bis(N-ethyl-N-decyldithiocarbamate),
2,5-dimethylbicyclo(2.2.1)heptyl-2,6-bis(N-ethyl-N-decyldithiocarbamate),
2,6-diethylbicyclo(2.2.1)heptyl-2,6-bis(N-ethyl-N-dodecyldithiocarbamate),
1,3,5-trimethylbicyclo(2.2.1)heptyl-2,6-bis(N-methyl-N-ethyldithiocarbamate),
2,4,6-triethylbicyclo(2.2.1)heptyl-2,6-bis(N-methyl-N-octyldithiocarbamate),
1,4,5,6,7,7-hexamethylbicyclo(2.2.1)heptyl-2,6-bis(N-ethyl-N-hexyldithiocarbamate),
7,7-dimethylbicyclo(2.2.1)heptyl-2,6-bis(N-ethyl-N-dodecyldithiocarbamate),
bicyclo(2.2.1)heptyl-2,6-bis(N,N-diethenyldithiocarbamate),
bicyclo(2.2.1)heptyl-2,6-bis(N,N-dipropenyldithiocarbamate),
bicyclo(2.2.1)heptyl-2,6-bis(N,N-dibutenyldithiocarbamate),
bicyclo(2.2.1)heptyl-2,6-bis(N,N-dihexenyldithiocarbamate),
bicyclo(2.2.1)heptyl-2,6-bis(N,N-didecenyldithiocarbamate),
1,4,5,6,7,7-hexaethylbicyclo(2.2.1)heptyl-2,6-bis(N,N-diethenyldithiocarbamate),
7,7-diisopropylbicyclo(2.2.1)heptyl-2,6-bis(N,N-dibutenyldithiocarbamate),
1,4-dimethylbicyclo(2.2.1)heptyl-2,6-bis(N,N-diethenyldithiocarbamate),
3,5-dimethylbicyclo(2.2.1)heptyl-2,6-bis(N,N-diethenyldithiocarbamate),
1,4-diethylbicyclo(2.2.1)heptyl-2,6-bis(N,N-diethenyldithiocarbamate),
3,5-diethylbicyclo(2.2.1)heptyl-2,6-bis(N,N-diethenyldithiocarbamate),
2,4-diisopropylbicyclo(2.2.1)heptyl-2,6-bis(N,N-diethenyldithiocarbamate),
2,4-dioctylbicyclo(2.2.1)heptyl-2,6-bis(N,N-diethenyldithiocarbamate),
2,4-didecylbicyclo(2.2.1)heptyl-2,6-bis(N,N-dipropenyldithiocarbamate),
2,5-dimethylbicyclo(2.2.1)heptyl-2,6-bis(N,N-dibutenyldithiocarbamate),
2,6-dimethylbicyclo(2.2.1)heptyl-2,6-bis(N,N-dihexenyldithiocarbamate),
1,3,5-trimethylbicyclo(2.2.1)heptyl-2,6-bis(N,N-didecenyldithiocarbamate),
2,4,6-triethylbicyclo(2.2.1)heptyl-2,6-bis(N,N-didodecenyldithiocarbamate),
bicyclo(2.2.1)heptyl-2,6-bis(N-ethenyl-N-propenyldithiocarbamate),
bicyclo(2.2.1)heptyl-2,6-bis(N-ethenyl-N-hexenyldithiocarbamate),
1,4-dimethylbicyclo(2.2.1)heptyl-2,6-bis(N-ethenyl-N-hexenyldithiocarbamate),
1,4-dioctylbicyclo(2.2.1)heptyl-2,6-bis(N-ethenyl-N-hexenyldithiocarbamate),
3,5-diethylbicyclo(2.2.1)heptyl-2,6-bis(N-ethenyl-N-decenyldithiocarbamate),
1,3,5-trimethylbicyclo(2.2.1)heptyl-2,6-bis(N-ethenyl-N-propenyldithiocarbamate),
1,4,5,6,7,7-hexamethylbicyclo(2.2.1)heptyl-2,6-bis(N-ethenyl-N-hexenyldithiocarbamate),
7,7-dimethylbicyclo(2.2.1)heptyl-2,6-bis(N-ethenyl-N-dodecenyldithiocarbamate),
bicyclo(2.2.1)heptyl-2,5-bis(N,N-dimethyldithiocarbamate),
bicyclo(2.2.1)heptyl-2,5-bis(N,N-diisopropyldithiocarbamate),
bicyclo(2.2.1)heptyl-2,5-bis(N,N-di-n-butyldithiocarbamate),
bicyclo(2.2.1)heptyl-2,5-bis(N,N-dihexyldithiocarbamate),
bicyclo(2.2.1)heptyl-2,5-bis(N,N-didodecyldithiocarbamate),
1,4-dimethylbicyclo(2.2.1)heptyl-2,5-bis(N,N-dimethyldithiocarbamate),
3,5-dimethylbicyclo(2.2.1)heptyl-2,5-bis(N,N-dimethyldithiocarbamate),
1,4-diethylbicyclo(2.2.1)heptyl-2,5-bis(N,N-dimethyldithiocarbamate),
3,5-diethylbicyclo(2.2.1)heptyl-2,5-bis(N,N-dimethyldithiocarbamate),
2,4-diisopropylbicyclo(2.2.1)heptyl-2,5-bis(N,N-di-n-butyldithiocarbamate),
2,4-dioctylbicyclo(2.2.1)heptyl-2,5-bis(N,N-di-n-butyldithiocarbamate),
2,4-didecylbicyclo(2.2.1)heptyl-2,5-bis(N,N-di-n-butyldithiocarbamate),
2,5-dimethylbicyclo(2.2.1)heptyl-2,5-bis(N,N-dihexyldithiocarbamate),
2,6-dimethylbicyclo(2.2.1)heptyl-2,5-bis(N,N-dioctyldithiocarbamate),
1,3,5-trimethylbicyclo(2.2.1)heptyl-2,5-bis(N,N-didecyldithiocarbamate),
2,4,6-triethylbicyclo(2.2.1)heptyl-2,5-bis(N,N-didodecyldithiocarbamate),
1,4,5,6,7,7-hexamethylbicyclo(2.2.1)heptyl-2,5-bis(N,N-di-n-butyldithiocarbamate),
7,7-dimethylbicyclo(2.2.1)heptyl-2,5-bis(N,N-dimethyldithiocarbamate),
bicyclo(2.2.1)heptyl-2,5-bis(N-methyl-N-ethyldithiocarbamate),
bicyclo(2.2.1)heptyl-2,5-bis(N-methyl-N-propyldithiocarbamate),
bicyclo(2.2.1)heptyl-2,5-bis(N-methyl-N-octyldithiocarbamate),
bicyclo(2.2.1)heptyl-2,5-bis(N-ethyl-N-hexyldithiocarbamate),
bicyclo(2.2.1)heptyl-2,5-bis(N-propyl-N-dodecyldithiocarbamate),
1,4-dimethylbicyclo(2.2.1)heptyl-2,5-bis(N-methyl-N-ethyldithiocarbamate),
3,5-dimethylbicyclo(2.2.1)heptyl-2,5-bis(N-methyl-N-propyldithiocarbamate),
1,4-diethylbicyclo(2.2.1)heptyl-2,5-bis(N-methyl-N-octyldithiocarbamate),
3,5-diethylbicyclo(2.2.1)heptyl-2,5-bis(N-ethyl-N-hexyldithiocarbamate),
2,4-dimethylbicyclo(2.2.1)heptyl-2,5-bis(N-ethyl-N-decyldithiocarbamate),
2,5-dimethylbicyclo(2.2.1)heptyl-2,5-bis(N-ethyl-N-decyldithiocarbamate),
2,6-diethylbicyclo(2.2.1)heptyl-2,5-bis(N-ethyl-N-dodecyldithiocarbamate),
1,3,5-trimethylbicyclo(2.2.1)heptyl-2,5-bis(N-methyl-N-ethyldithiocarbamate),
2,4,6-triethylbicyclo(2.2.1)heptyl-2,5-bis(N-methyl-N-octyldithiocarbamate),
1,4,5,6,7,7-hexamethylbicyclo(2.2.1)heptyl-2,5-bis(N-ethyl-N-hexyldithiocarbamate),
7,7-dimethylbicyclo(2.2.1)heptyl-2,5-bis(N-ethyl-N-dodecyldithiocarbamate), bicyclo(2.2.1)heptyl-2,5-bis(N,N-diethenyldithiocarbamate),
bicyclo(2.2.1)heptyl-2,5-bis(N,N-dipropenyldithiocarbamate),
bicyclo(2.2.1)heptyl-2,5-bis(N,N-dibutenyldithiocarbamate),
bicyclo(2.2.1)heptyl-2,5-bis(N,N-dihexenyldithiocarbamate),
bicyclo(2.2.1)heptyl-2,5-bis(N,N-didecenyldithiocarbamate),
1,4-dimethylbicyclo(2.2.1)heptyl-2,5-bis(N,N-diethenyldithiocarbamate),
3,5-dimethylbicyclo(2.2.1)heptyl-2,5-bis(N,N-diethenyldithiocarbamate),
1,4-diethylbicyclo(2.2.1)heptyl-2,5-bis(N,N-diethenyldithiocarbamate),
3,5-diethylbicyclo(2.2.1)heptyl-2,5-bis(N,N-diethenyldithiocarbamate),
2,4-diisopropylbicyclo(2.2.1)heptyl-2,5-bis(N,N-diethenyldithiocarbamate),
2,4-dioctylbicyclo(2.2.1)heptyl-2,5-bis(N,N-diethenyldithiocarbamate),
2,4-didecylbicyclo(2.2.1)heptyl-2,5-bis(N,N-dibutenyldithiocarbamate),
2,5-dimethylbicyclo(2.2.1)heptyl-2,5-bis(N,N-dibutenyldithiocarbamate),
2,6-dimethylbicyclo(2.2.1)heptyl-2,5-bis(N,N-dihexenyldithiocarbamate),
1,3,5-trimethylbicyclo(2.2.1)heptyl-2,5-bis(N,N-didecenyldithiocarbamate),
2,4,6-triethylbicyclo(2.2.1)heptyl-2,5-bis(N,N-didodecenyldithiocarbamate),
1,4,5,6,7,7-hexaethylbicyclo(2.2.1)heptyl-2,5-bis(N,N-diethenyldithiocarbamate),
7,7-diisopropylbicyclo(2.2.1)heptyl-2,5-bis(N,N-dibutenyldithiocarbamate),
bicyclo(2.2.1)heptyl-2,5-bis(N-ethenyl-N-propenyldithiocarbamate),
bicyclo(2.2.1)heptyl-2,5-bis(N-ethenyl-N-hexenyldithiocarbamate),
1,4-dimethylbicyclo(2.2.1)heptyl-2,5-bis(N-ethenyl-N-hexenyldithiocarbamate),
1,4-dioctylbicyclo(2.2.1)heptyl-2,5-bis(N-ethenyl-N-hexenyldithiocarbamate),
3,5-diethylbicyclo(2.2.1)heptyl-2,5-bis(N-ethenyl-N-decenyldithiocarbamate),
1,3,5-trimethylbicyclo(2.2.1)heptyl-2,5-bis(N-ethenyl-N-propenyldithiocarbamate),
1,4,5,6,7,7-hexamethylbicyclo2.2.1)heptyl-2,5-bis(N-ethenyl-N-hexenyldithiocarbamate),
7,7-dimethylbicyclo(2.2.1)heptyl-2,5-bis(N-ethenyl-N-dodecenyldithiocarbamate),
and the like.

Thus, in one aspect of the invention there is provided an antiwear and antioxidant compound or mixture of compounds having the general formulae:

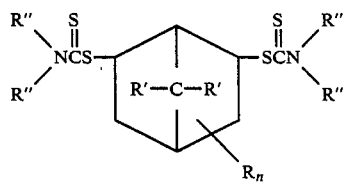

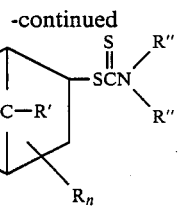

wherein R is an alkyl group containing from 1 to 20 carbon atoms, n represents a number selected from the class consisting of zero and the integers from 1 through 6, R' represents a member selected from the group consisting of the hydrogen atom and those groups represented by R, and R" is an aliphatic hydrocarbon group.

The additives of the invention are readily prepared by reacting a secondary monoamine of the general formula:

R"—NH—R"

in which R" is an aliphatic hydrocarbon group, preferably an aliphatic hydrocarbon group containing up to 12 carbon atoms with carbon disulfide and a bicyclo(2.2.1)hepta-2,5-diene having the general formula:

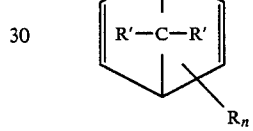

wherein R and R' are as hereinbefore defined.

As the diene reactant, there may be used bicyclo(2.2.1)hepta-2,5-diene itself or its alkyl substituted analogs. Examples of this class of reactants which may be used to prepare the novel compounds of the invention include 1,4-dimethyl and 1,4-diethylbicyclo(2.2.1)hepta-2,5-diene, 3,5-dimethyl and 3,5-diethylbicyclo(2.2.1)hepta-2,5-diene, 2,4-diisopropyl, 2,4-dioctyl and 2,4-didecylbicyclo(2.2.1)hepta-2,5-diene, 2,5-dimethylbicyclo(2.2.1)hepta-2,5-diene, 2,6-dimethylbicyclo(2.2.1)hepta-2,5-diene, 1,3,5-trimethylbicyclo(2.2.1)hepta-2,5-diene, 2,4,6-triethylbicyclo(2.2.1)hepta-2,5-diene, 7,7-dimethylbicyclo(2.2.1)hepta-2,5-diene, 1,2,3,4-tetramethylbicyclo(2.2.1)hepta-2,5-diene, 1,2,3,4-tetrabutylbicyclo(2.2.1)hepta-2,5-diene, 1,2,3,4,7,7-hexamethylbicyclo(2.2.1)hepta-2,5-diene, and the like.

As stated above, the amine reactants of the present invention can be represented by the formula:

R"—NH—R"

in which R" is an aliphatic hydrocarbon group, preferably an aliphatic hydrocarbon group containing up to 12 carbon atoms such as the alkyl and alkenyl groups and their substitution derivatives. It is preferred that the group designated by the symbol R" be an unsubstituted lower alkyl group containing not more than about 8 carbon atoms. Examples of this group include the methyl, ethyl, propyl, hexyl, octyl, decyl, dodecyl, ethenyl, propenyl, butenyl, hexenyl, octenyl and dodecenyl groups.

Specific examples of suitable amine reactants which can be used in the practice of the present invention include dimethylamine, diethylamine, di-n-propylamine, diisopropylamine, di-n-butylamine, di-sec-butylamine, diisobutylamine, di-tert-butylamine, dipentylamine, dihexylamine, dioctylamine, didecylamine, didodecylamine, N-methyl-N-ethylamine, N-methyl-N-propylamine, N-methyl-N-octylamine, N-ethyl-N-hexylamine, N-ethyl-N-decylamine, N-propyl-N-dodecylamine, diethenylamine, dipropenylamine, dibutenylamine, dihexenylamine, dioctenylamine, didecenylamine, N-ethenyl-N-propenylamine, N-ethenyl-N-hexenylamine, N-ethenyl-N-decenylamine, and the like.

The reaction is effected by mixing together the reactants and maintaining the mixture at a temperature high enough to promote the reaction at a reasonable rate, but not so high as to cause decomposition. A useful range is from about 70°–100° C. The optimum temperature generally lies within the range of from about 50°–90° C. In many cases it will be found that the reaction is exothermic in character.

The reactants are employed in approximately stoichiometric proportions. This limitation is not critical however. Typically, a slight excess of carbon disulfide is used in order to compensate for any loss of carbon disulfide which may occur through volatilization during the course of the reaction. This helps to insure maximum product yield. The reaction can be conveniently carried out by merely mixing and heating the reactants. It is preferred, however, to add the amine reactant slowly, in dropwise fashion, to a mixture of the carbon disulfide and bicyclo(2.2.1)hepta-2,5-diene reactants in order to suppress unwanted amine salt formation which can occur if the reactants are brought into immediate contact.

The reaction can be carried out in an inert atmosphere if desired, but the use of an inert atmosphere above the reaction mixture is not required.

The reaction should be carried out for a time sufficient to form a substantial amount of product. This is usually accomplished in from 0.5 to 12 hours. A more useful time range is from about 2 to 4 hours.

The process of the present invention produces mixtures containing both 2,6-bis(N,N-dihydrocarbyldithiocarbamate) and 2,5-bis(N,N-dihydrocarbyldithiocarbamate). These mixtures are effective in conveying both antioxidant and antiwear properties to lubricating oil containing them.

Thus, in accordance with another aspect of the invention, there is provided a process for preparing an oil-soluble compound or mixtures of compounds having the formulae:

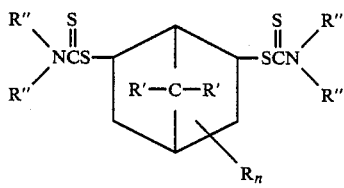

(A)

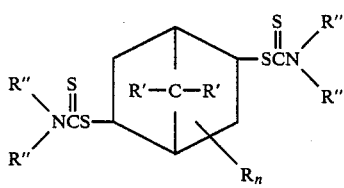

(B)

wherein R is an alkyl group containing from 1 to 20 carbon atoms, n represents a member selected from the class consisting of zero and the integers from 1 through 6, R' represents a member selected from the group consisting of the hydrogen atom and those groups represented by R, and R" is an aliphatic hydrocarbon group by reacting a bicyclo(2.2.1)hepta-2,5-diene having the general formula:

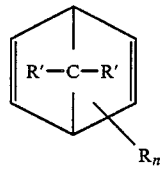

(C)

wherein R and R' are as hereinbefore defined with carbon disulfide and an amine having the general formula:

R"—NH—R"

where R" is an aliphatic hydrocarbon group.

Preferably, the lubricating compositions of the present invention comprise from 0.1% to 10%, more preferably, 0.25% to 5% by weight of the oil-soluble products of foregoing formulae (A) and (B) and the lubricating oil may be any of the well-known mineral or synthetic oils of appropriate viscosity characteristics.

It will be understood that the lubricating compositions of the present invention may also contain, if desired, conventional lubricant additives such as ancillary antioxidants and antiwear additives (preferably ashless), corrosion inhibitors, dispersants, detergents, thickeners, pour-point depressants and viscosity index improvers.

Hence, in accordance with another aspect of the present invention there is provided a lubricating composition containing a major amount of lubricating oil and a minor antiwear-antioxidant amount of a compound or mixtures of compounds having the general formulae:

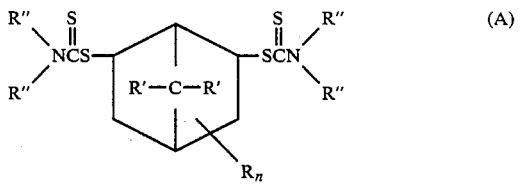

(A)

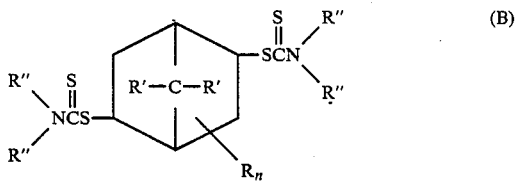

(B)

wherein R is an alkyl group containing from 1 to 20 carbon atoms, n represents a number selected from the class consisting of zero and the integers from 1 through 6, R' represents a member selected from the group consisting of the hydrogen atom and those groups represented by R, and R" is an aliphatic hydrocarbon group.

The additives of the present invention may also be conveniently prepared as a concentrate consisting of a concentrated solution of a major amount of the additives and a minor amount of a mineral or synthetic lubricating oil, or as an additive package consisting of a concentrated solution in mineral oil or synthetic oil of a major amount of a combination of the additives with one or more conventional additives. Such concentrates and packages are frequently very convenient forms in which to handle and transport additives and are diluted with further quantities of oil, and optionally blended with further additives, before use.

Thus, in accordance with a further aspect of the invention, there is provided a solution comprising a major amount of a compound or mixture of compounds having the formulae (A) or (B) and a minor amount of a lubricating oil. One or more conventional additives may be combined with the compounds of formulae (A) and (B).

The following example will serve to illustrate the manner in which the antiwear and antioxidant additives are prepared but not to limit in any respect the scope of the invention claimed.

EXAMPLE I

To a 250 milliliter reaction vessel equipped with a stirrer, thermometer and condenser was added 18.4 grams (0.2 mole) of bicyclo(2.2.1)hepta-2,5-diene and 44.4 grams (0.58 mole) of carbon disulfide. Di-n-butylamine (51.6 grams; 0.4 mole) was added slowly to the reaction vessel and the temperature started to rise due to exotherm. Reflux of a clear liquid was observed. Amine addition was completed in about 17 minutes and the resulting mixture was heated to 70° C. from 63° C. and maintained at that temperature for 1 hour. The volatile liquid was removed by vacuum distillation at 70° C. for 15 minutes. A dark orange-brown liquid (94.5 grams) was obtained. Analysis by NMR served to identify the product as a mixture containing bicyclo(2.2.1-)heptyl-2,6-bis(N,N-di-n-butyldithiocarbamate) and bicyclo(2.2.1)heptyl-2,5-bis(N,N-di-n-butyldithiocarbamate).

The antiwear properties of the lubricating oil compositions of the present invention were determined in a 4-Ball Wear Test. This test is conducted in a device comprising four steel balls, three of which are in contact with each other in one plane in a fixed triangular position and a reservoir containing the test sample. The fourth ball is above and in contact with the other three. In conducting the test, the upper ball is rotated while it is pressed against the other three balls while pressure is applied by weight and lever arms. The diameter of the scar on the three lower balls is measured by means of a low-power microscope, and the average diameter measured in two directions on each of three lower balls is taken as a measure of the antiwear characteristics of the oil. A larger scar diameter means more wear. The balls were immersed in base lube oil containing the test additives. Applied load was 40 kg and rotation was at 1800 rpm for 30 minutes at 130° F. Tests were conducted with base oil alone (Exxon 80W-90 mineral oil) and with base oil containing 0.5 wt. % of the additive of Example I. Results are given in the following table.

| Oil Formulation | Scar Diameter (mm) |
| --- | --- |
| Base Oil | 0.663 |
| Base Oil + 0.5 wt. % additive (Example I) | 0.483 |

The results in the table show that lubricating oil containing the additives of the present invention gave a scar diameter significantly less than that of the base oil alone.

Hot Oil Oxidation Test were carried out to demonstrate the antioxidant effectiveness of the present additives. In these tests, fully formulated mineral lubricating oil samples were prepared both with and without the additive. The oil is placed in a test cell together with 0.3 cubic centimeter of a catalyst composition prepared by dissolving 6.65 grams of ferric acetylacetonate and 0.6 gram of cupric acetylacetonate in 100 grams of xylene. The cell was heated to 160° C. and dry air blown through the heated oil for 48 hours at a rate of 10 liters/hour. The percent viscosity increase was measured at 40° C. The following results were obtained:

| Additive | Percent Viscosity Increase |
| --- | --- |
| None | 64.7 |
| Example I (0.26 wt. % based on total weight of the oil) | 20.5 |

These results demonstrate that the additive compounds of the invention are effective antioxidants.

What is claimed:

1. A lubricating composition containing a major amount of lubricating oil and a minor antiwear-antioxidant amount of an additive compound or mixtures of compounds having the general formulae:

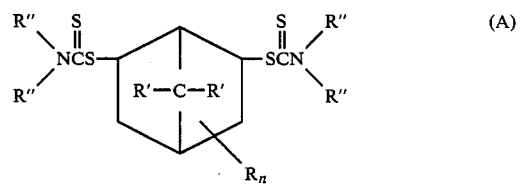

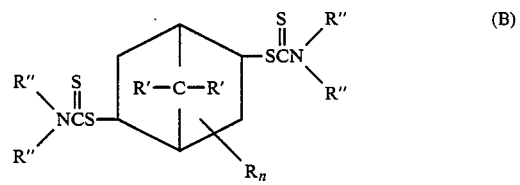

wherein R is an alkyl group containing from 1 to 20 carbon atoms, n represents a number selected from the class consisting of zero and the integers from 1 through 6, R' represents a member selected from the group consisting of the hydrogen atom and those groups represented by R, and R" is an aliphatic hydrocarbon group.

2. A lubricating composition of claim 1 in which the symbol R" represents an alkyl group.

3. A lubricating composition of claim 2 in which the symbol R" represents an alkyl group having from 1 to 12 carbon atoms.

4. A lubricating composition of claim 1 wherein said compound is a bicyclo(2.2.1)heptyl-2,6-bis(N,N-dihydrocarbyldithiocarbamate).

5. A lubricating composition of claim 1 wherein said compound is bicyclo(2.2.1)heptyl-2,6-bis(N,N-dimethyldithiocarbamate).

6. A lubricating composition of claim 1 wherein said compound is bicyclo(2.2.1)heptyl-2,6-bis(N,N-di-n-butyldithiocarbamate).

7. A lubricating composition of claim 1 wherein said compound is bicyclo(2.2.1)heptyl-2,6-bis(N,N-didodecyldithiocarbamate).

8. A lubricating composition of claim 1 wherein said compound is 3,5-dimethylbicyclo(2.2.1)heptyl-2,6-bis(N,N-di-n-butyldithiocarbamate).

9. A lubricating composition of claim 1 wherein said compound is 1,3,5-trimethylbicyclo(2.2.1)heptyl-2,6-bis(N,N-didecyldithiocarbamate).

10. A lubricating composition of claim 1 wherein said compound is 7,7-dimethylbicyclo(2.2.1)heptyl-2,6-bis(N,N-dimethyldithiocarbamate).

11. A lubricating composition of claim 1 wherein said compound is 1,4,5,6,7,7-hexamethylbicyclo(2.2.1)heptyl-2,6-bis(N,N-dimethyldithiocarbamate).

12. A lubricating composition of claim 1 wherein said compound is bicyclo(2.2.1)heptyl-2,6-bis(N,N-diethenyldithiocarbamate).

13. A lubricating composition of claim 1 wherein said compound is bicyclo(2.2.1)heptyl-2,6-bis(N-ethenyl-N-propenyldithiocarbamate).

14. A lubricating composition of claim 1 wherein said compound is bicyclo(2.2.1)heptyl-2,5-bis(N,N-dihydrocarbyldithiocarbamate).

15. A lubricating composition of claim 1 wherein said compound is bicyclo(2.2.1)heptyl-2,5-bis(N,N-dimethyldithiocarbamate).

16. A lubricating composition of claim 1 wherein said compound is bicyclo(2.2.1)heptyl-2,5-bis(N,N-di-n-butyldithiocaramate).

17. A lubricating composition of claim 1 wherein said compound is bicyclo(2.2.1)heptyl-2,5-bis(N,N-didodecyldithiocarbamate).

18. A lubricating composition of claim 1 wherein said compound is 3,5-dimethylbicyclo(2.2.1)heptyl-2,5-bis(N,N-di-n-butyldithiocarbamate).

19. A lubricating composition of claim 1 wherein said compound is 1,3,5-trimethylbicyclo(2.2.1)heptyl-2,5-bis(N,N-didecyldithiocarbamate).

20. A lubricating composition of claim 1 wherein said compound is 7,7-dimethylbicyclo(2.2.1)heptyl-2,5-bis(N,N-dimethyldithiocarbamate).

21. A lubricating composition of claim 1 wherein said compound is 1,4,5,6,7,7-hexamethylbicyclo(2.2.1)heptyl-2,5-bis(N,N-dimethyldithiocarbamate).

22. A lubricating composition of claim 1 wherein said compound is bicyclo(2.2.1)heptyl-2,5-bis(N-methyl-N-ethyldithiocarbamate).

23. A lubricating composition of claim 1 wherein said compound is bicyclo(2.2.1)heptyl-2,5-bis(N,N-diethenyldithiocarbamate).

24. A lubricating composition of claim 1 wherein said compound is bicyclo(2.2.1)heptyl-2,5-bis(N-ethenyl-N-propenyldithiocarbamate).

25. A lubricating composition of claim 1 wherein said mixture of compounds is a mixture of bicyclo(2.2.1)heptyl-2,6-bis(N,N-di-n-butyldithiocarbamate) and bicyclo(2.2.1)heptyl-2,5-bis(N,N-di-n-butyldithiocarbamate).

26. A lubricating composition of claim 1 which comprises from 0.1 to 10 percent by weight of the additive compound.

27. A process for preparing an oil-soluble compound or mixtures of compounds having the general formulae:

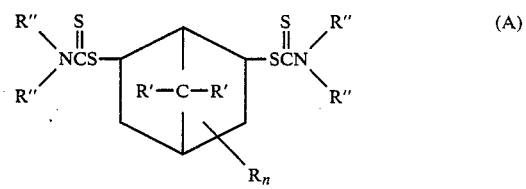

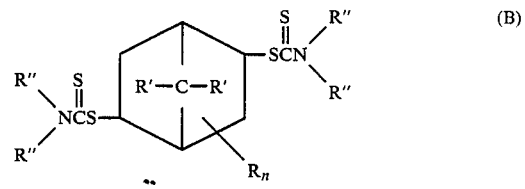

wherein R is an alkyl group containing from 1 to 20 carbon atoms, n represents a number selected from the class consisting of zero and the integers from 1 through 6, R' represents a member selected from the group consisting of the hydrogen atom and those groups represented by R, and R" is an aliphatic hydrocarbon group which comprises reacting a bicyclo(2.2.1)hepta-2,5-diene having the general formula:

wherein R and R' are as defined above with carbon disulfide and an amine having the general formula:

where R" is an aliphatic group havng up to 12 carbon atoms.

28. The process according to claim 27 wherein said reaction is carried out at a temperature of from about 30°–100° C.

29. The process according to claim 27 wherein said bicyclo(2.2.1)hepta-2,5-diene, carbon disulfide and amine are reacted together in equal mole quantities.

30. The process according to claim 27 where said amine is di-n-butylamine and said bicyclo(2.2.1)hepta-2,5-diene is bicyclo(2.2.1)hepta-2,5-diene.

31. A concentrate for addition to a lubricating composition, said concentrate comprising a minor amount of a mineral or synthetic oil and a major amount of a compound or mixture of compounds having the general formulae:

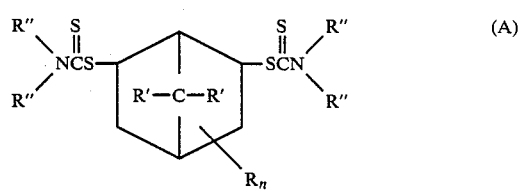

-continued

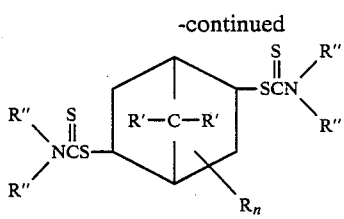

wherein R is an alkyl group containing from 1 to 20 carbon atoms, n represents a member selected from the class consisting of zero and the integers from 1 through 6, R' represents a member selected from the group consisting of the hydrogen atom and those groups represented by R, and R" is an aliphatic hydrocarbon group.

32. A concentrate according to claim 31 in which the symbol R" represents an alkyl group.

33. A concentrate according to claim 32 in which the symbol R" represents an alkyl group having from 1 to 12 carbon atoms.

34. A concentrate according to claim 31 wherein said compound is bicyclo(2.2.1)heptyl-2,6-bis(N,N-dihydrocarbyldithiocarbamate).

35. A concentrate according to claim 31 wherein said compound is bicyclo(2.2.1)heptyl-2,6-bis(N,N-dimethyldithiocarbamate).

36. A concentrate according to claim 31 wherein said compound is bicyclo(2.2.1)heptyl-2,6-bis(N,N-di-n-butyldithiocarbamate).

37. A concentrate according to claim 31 wherein said compound is bicyclo(2.2.1)heptyl-2,5-bis(N,N-di-n-butyldithiocarbamate).

38. A concentrate according to claim 31 wherein said compound is bicyclo(2.2.1)heptyl-2,5-bis(N,N-di-n-butyldithiocarbamate).

* * * * *

UNITED STATES PATENT AND TRADEMARK OFFICE
CERTIFICATE OF CORRECTION

PATENT NO. : 4,836,942

DATED : June 6, 1989

INVENTOR(S) : William Yuk-Lun Lam

It is certified that error appears in the above-identified patent and that said Letters Patent is hereby corrected as shown below:

Column 5, line 24 reads "N,N-dibutenyl" and should read
-- N,N-dipropenyl --.

Signed and Sealed this

Twentieth Day of March, 1990

Attest:

JEFFREY M. SAMUELS

Attesting Officer

Acting Commissioner of Patents and Trademarks